United States Patent [19]

Pfreundschuh

[11] Patent Number: 5,698,396
[45] Date of Patent: Dec. 16, 1997

[54] METHOD FOR IDENTIFYING AUTO-IMMUNOREACTIVE SUBSTANCES FROM A SUBJECT

[75] Inventor: Michael Pfreundschuh, Homburg/Saar, Germany

[73] Assignee: Ludwig Institute For Cancer Research, New York, N.Y.

[21] Appl. No.: 479,328

[22] Filed: Jun. 7, 1995

[51] Int. Cl.$^6$ .................. C12Q 1/68; C12Q 1/70; G01N 33/53; G01N 33/574
[52] U.S. Cl. .................. 435/6; 435/5; 435/7.1; 435/7.23
[58] Field of Search ............. 435/6, 5, 7.1, 7.2, 435/7.23

[56] References Cited

U.S. PATENT DOCUMENTS

| | | | |
|---|---|---|---|
| 5,571,710 | 11/1996 | Barnett et al. | 435/240.1 |
| 5,583,024 | 12/1996 | McElroy et al. | 135/189 |
| 5,583,046 | 12/1996 | Valenta et al. | 435/320.1 |
| 5,585,258 | 12/1996 | Houghton et al. | 435/219 |
| 5,585,464 | 12/1996 | Prakash | 530/350 |
| 5,587,304 | 12/1996 | Barre et al. | 435/139 |

OTHER PUBLICATIONS

Breiteneder et al. (1989) EMBO J. 8:1935–38.
de Wet et al. (1984) DNA 3:437–447.

*Primary Examiner*—W. Gary Jones
*Assistant Examiner*—Amy Atzel
*Attorney, Agent, or Firm*—Felfe & Lynch

[57] ABSTRACT

The invention describes methods for identifying a molecule of interest, as well as nucleic acid molecules which encode it, and binding partners for it. A cDNA library from a cell expressing the target is prepared, and expressed in host cells. Lysates of the host cells are screened with a sample, treated to remove interfering binding partners. The treatment involves contact of the sample to lysates of untransfected host cells, and host cells transfected or transformed with the same vector used to make the cDNA library. Also a part of the invention are antigens and cDNA identified using the methodology.

16 Claims, 4 Drawing Sheets

FIG. 4

ORIGIN

```
   1 ATCTGCAGAA TTCGGCTTCG ATCTAGAACT AGTGGATCCC CCGGGCTGCA GGAATTCGGC
  61 ACGAGCGGTT CCAAGTGGAC TTATTTGGT CCTGATGGGG AGAATAGCTG GTCCAAGAAG
 121 TACCCGTCGT GTGGGGGCCT GCTGCAGTCC CCCATAGACC TGCACAGTGA CATCCTCCAG
 181 TATGACGCCA GCCTCACGCC CCTCGAGTTC CAAGGCTACA ATCTGTCTGC CAACAAGCAG
 241 TTTCTCCTGA CCAACAATGG CCATTCAGTG AAGCTGAACC TGCCCTCGGA CATGCACATC
 301 CAGGGCCTCC AGTCTCGCTA CAGTGCCACG CAGCTGCACC TGCACTGGGG GAACCCGAAT
 361 GACCCGCACG GCTCTGAGCA TACCGTCAGC GGACAGCACT TCTCCGCCGA GCTGCACATT
 421 GTCCATTATA ACTCAGACCT TTATCCTGAC GACAG?ACTG CCAGCAACAA GTCAGAAGAC
 481 CTCGCTGTCC TGGGTGCTCT CATTGAGATG GGCTCCTTCA ATCCGTCCTA TGACAAGATC
 541 TTCAGTCACC TTCAACATGT AAAGTACAAA GGCCAGGAAG CATTCGTCCC GGGATTCAAC
 601 ATTGAAGAGC TGCTTCCGGA GAGGACCGCT GAATATTACC GCTACCGGGG GTCCCTGATC
 661 ACACCCCCTT GCAACCCCAC TGTGCTCTGG GAAACCCCGT GCAAATTTCC
 721 CAGGAGCAGC TGCTGGCTTT GGAGACAGCC CTGTACTGCA CACACATGGA CGACCCTTCC
 781 CCCAGAGAAA TGATCAACAA CT?CCGGCAG GTCCAGAAGT TCG?TGAGAG GCTGGTATAC
 841 ACCTCCTTCT C?CAAGTGCA AGTCTGTACT GCGGCAGGAC TGAGTCTGGG CATCATCCTC
 901 TCACTGGCCC TGGCTGGCAT TCTTGGCCAT TGTATTGTGG TGGTGGTGTC CATTTGGCTT
 961 TTCAGAAGGA AGAGTA?CCC C?AAAGGTGA TAACAAGGGA GTCATTTACA AGCCA?CCAC
1021 CAAGATGGAG ACTGAGGCCC ACGCTTGAGG TCCCCGGAGC TCCCGGGCAC ATCCAGGAAG
1081 GACCTTGCTT TTGGACCCTA CACACTTCGG CTCTCTGGAC ACTTGCGACA CCTCAAGGTG
1141 TTTCTCTGTAG CTCAATCTGC AAACATGCCA GGCCTCAGGG ATCCTCTGCT
//
```

METHOD FOR IDENTIFYING AUTO-IMMUNOREACTIVE SUBSTANCES FROM A SUBJECT

FIELD OF THE INVENTION

This invention relates to methodologies for identifying molecules of interest. In particularly preferred embodiments, the invention relates to the identification of molecules associated with pathological conditions such as cancer, (melanoma or renal cancer, e.g.), Hodgkin's Disease, autoimmune diseases and so forth. Also a part of the invention are the isolated molecules found as a result of the inventive method. These molecules include, inter alia, protein-containing molecules, isolated nucleic acid molecules encoding these, and antibodies which specifically bind to the protein-containing molecules. For convenience, the method described herein will be referred to as "serological fishing".

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens, in e.g., human tumors. These will be referred to as the genetic approach and the biochemical approach. The genetic approach is exemplified by, e.g., dePlaen et al., Proc. Natl. Acad. Sci. USA. 85: 2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., Falk et al., Nature 351: 290 (1991); and Kawakami et al., Nature 369: 69 (1994) both of which are incorporated by reference, is based on acidic elution of peptides which have bound to MHC-I molecules of tumor cells, followed by reversed-phase high performance liquid Chromatogaphy (HPLC). Antigenic peptides are identified after they bind to empty MHC-I molecules of mutant cell lines, defective in antigen processing, and induction of specific reactions in cytotoxic T-lymphocytes. These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; second, they depend on the establishment of cytotoxic T cell lines (CTLs) with predefined specificity; and third, their relevance in vivo for the course of the pathology or disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994), Kawakami et al., Proc. Natl. Acad. Sci. USA 91: 3515–3519 (1994).

It would be desirable to have available a method which can be used not only for detection of tumor-associated antigens, but to determine molecules associated with any abnormal or pathological condition. Such a method would also facilitate the identification of such molecules, thereby enabling their use on the generation of, e.g., antibodies, cytolytic T cells, and so forth.

It is therefore the purpose of the present invention to develop a method for the simple detection and molecular characterization of antigens in human tissues, especially in tumor cells, which are useful in the molecular diagnosis of diseases and/or for immunotherapy and gene therapy of infectious, autoimmune and malignant diseases. The invention is delineated in the disclosure which follows.

BRIEF DESCRIPTION OF THE FIGURES

FIG. 4 shows the translated region of the gene coding for HOM-RCC-313.

DETAILED DESCRIPTION OF PREFERRED EMBODIMENTS

Figure 1:
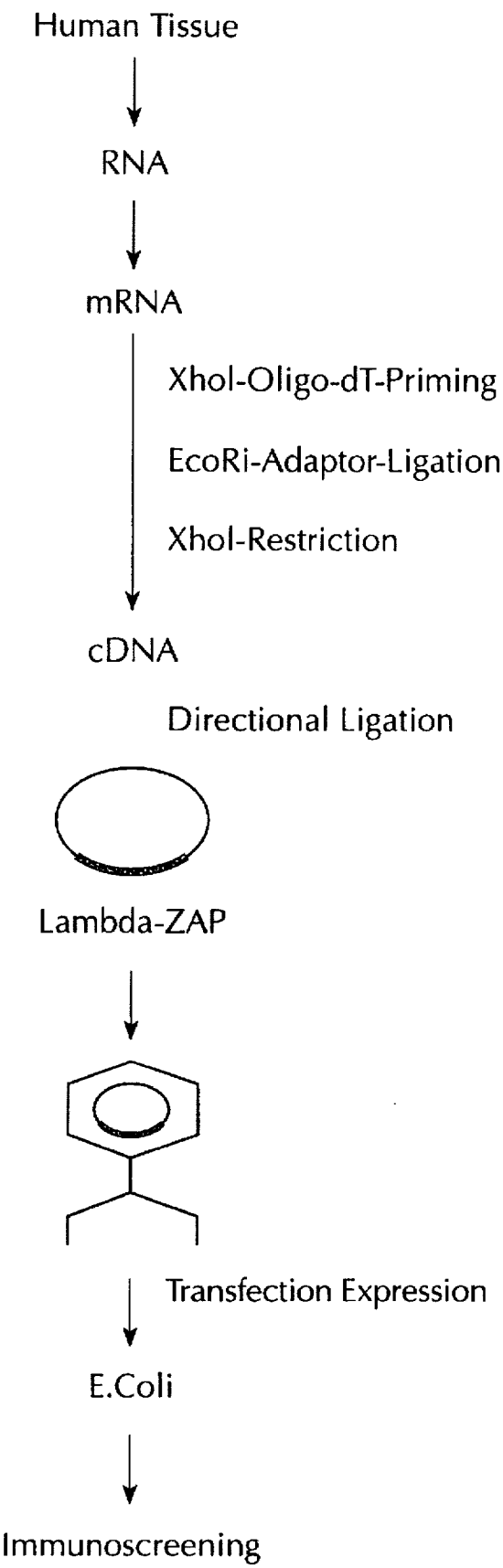
FIG. 1 shows the principles of the approach of the invention.

The following disclosure describes a methodology referred to as serological fishing. In it, a cell sample is taken from a subject afflicted with a pathological condition. The cells preferably are exemplary of the pathology. For example, if the subject has melanoma, the cells are melanoma cells. If the subject is suffering from a neural disorder, e.g., then the cells are preferably a sample of the afflicted cells. This approach is warranted because the afflicted cells are most probably the best source of protein-containing molecules of interest, i.e., such molecules which are specifically associated with the pathological condition of interest.

Note that cells representative of pathological conditions are not the only cells which may be used in the inventive method. It is very important, e.g., to ascertain those cellular "markers" associated with differentiation and maturation of cells, for example. The example of hematopoietic stem cells comes to mind. Similarly, the invention contemplates the isolation of, e.g., receptor molecules for specific ligands. In effect, one can assay for the presence of any molecule of interest using this methodology.

The cells chosen are then used to prepare a library of complementary DNA (i.e., "cDNA"). This methodology is well known to the skilled artisan, and need not be reiterated here. It is, of course, based upon the established fact that if proteins are expressed by the cells, then messenger RNA (mRNA) must be present. These mRNA molecules are not long lived, and are unstable, so they are not practical to work with. The stability brought to the molecules when cDNA is used is very helpful to the method.

Once the cDNA is made, it is used to construct a vector library. In short, carrier vectors are treated, such as by cutting and splicing, to receive molecules of cDNA. The choice of vector may vary, as the skilled artisan is well familiar with many such examples.

Especially preferred are virus based vectors. In the case of eukaryotic cells, retrovirus or adenovirus based vectors are preferred. Such vectors contain all or a part of a viral genome, such as long term repeats ("LTRs"), promoters (e.g., CMV promoters, SV40 promoter, RSV promoter), enhancers, and so forth. When the host cell is a prokaryote. Then bacterial viruses, or phages, are preferred. Exemplary of such vectors are vectors based upon, e.g., lambda phage. In any-case, the vector may comprise elements of more than one virus.

The resulting vectors are transfected or transformed into a host cell, which may be eukaryotic or prokaryotic.

Any cell normally used for transfection or transformation may be used in the protocol. Preferred materials include strains of $E.\ coli$, CHO cells such as CHO-1, COS cells such as COS-7, and so forth. Similarly, yeast cells, e.g., strains of Saccharomyces, strains of Pseudomonas, such as strains of $Pseudomonas\ aeruginosa$, $Bacillus\ bacteria$, $Spodoptera\ frugiperda$, a well known insect host cell, and so forth, may all be used.

Once the recipient cells receive the vectors, they are cultivated so as to express foreign, protein containing molecules. "Protein-containing" is used herein because, while prokaryotes express only proteins, eukaryotic cells are well known for their ability to post-translationally modify proteins, so as to produce glycoproteins, lipoproteins, e.g. It must also be borne in mind that "protein containing" as used herein, also encompasses peptides, such as the peptides presented by MHC molecules.

The processes now described below take place independently of the process described above, and no chronological relationship between the two facets of the invention is intended.

In pathological conditions such as cancer and, e.g., autoimmune diseases, there is some immune reaction to molecules associated with the pathology. This reaction can include an antibody response, B cell proliferation, proliferation of specific T cell subpopulations, increases in cytokine production, and so forth. The molecules and cells associated with the response may be found in body fluids of a subject, such as his or her serum. The immune responders will react with the molecule of interest whether it is produced recombinantly or autologously. The problem is to find them. As the examples show, this is done in a unique way. First, the body fluid, or other sample of interest, is reacted with a sample of the same host cells used for transfection or transformation. In this first step, the host cells are not transfected or transformed. The effect of this is to strip any immunogenic binding partners specific for the host cell rather than the targeted molecule. This step is necessary because, as was pointed out, supra, the host cell may be one against which the subject has developed an immune respone at some point. This first stripping removes these immune components.

A second stripping step is then carried out. In this step, the previously stripped sample is now reacted with a sample of the same host cell as was described supra, this time having been transfected or transformed with the carrier vector lacking cDNA from the subject. The reason for this second stripping step is an observation made by the present inventors not reported in the literature. The materials used as vectors, such as phages, viruses, etc., are useful because they naturally infect cells. Thus, $E.\ coli$ which inhabit the lower intestine of humans are infected with lambda phage. It had not been considered, previously, that the immune response to $E.\ coli$ includes a response to these infectious agents. Thus, applicants have surprisingly, achieved an ability to remove interfering immune components to an unprecedented degree by carrying out the two stripping steps. As noted, the first is against untransfected or untransformed host cells. The second is against host cells transfected or transformed with a vector which does not carry cDNA, wherein the vector is immunologically equivalent to the vector used to carry cDNA, as described supra.

It is especially preferred to carry out each of these stripping steps using a plurality of similar, but different procedures. The experiments which follow, for example, show absorption on a solid phase column, and then absorption on nitrocellulose paper. Applicants do not wish to be bound by any theory as to why the use of two similar but different protocols produces the results described herein. It is to be borne in mind, hereafter, that whenever "contacting a sample" is used herein, it is not to be limited to one contact step only, but may refer to more than one, preferably different contact protocols designed to remove interfering binding partners from a sample under scrutiny.

It should be understood that these stripping steps may be done completely independently of the steps used to prepare the cDNA library. For example, if the test for an antigen is to be done at day "0", the stripping of sample may be done the day before, a week before, and so forth. One can also "bank" stripped sample from a donor or subject for future use.

The sample used is preferably serum, but need not be. Any sample which contains immunogenic binding partners may be so used.

In the next step of the method, lysed, transfected cells carrying the cDNA and expressing heterologous protein are contacted with the twice stripped sample. This sample should only contain immune components specific for the heterologous protein, and should bind thereto. This binding is facilitated if the cell lysates have been immobilized via contact to, e.g., activated filter paper, a solid phase column, etc., but this solid phase binding is not necessary, as the art will surely recognize that many, varied forms of assays are available for identifying a molecule of interest.

Once the immune component binds to the target molecule, a further step is desirably, but not necessarily, carried out. This additional step involves the use of some binding partner for the first immune component, such as anti-IgG, carrying an identifiable label. The label may be a dye, an enzyme, a gold particle, a radiolabel, or any of the standard labels used in immunoassays.

Once identification is carried out, the immune components are removed, leaving the target molecule. The target molecule is then studied, using any of the standard methodologies in the art.

The artisan will note that the methodology also results in isolation of immune components which bind to the molecule of interest. Thus, in another aspect of the invention one can isolate antibodies, e.g., which are specific binding partners for the molecule of interest.

Yet another immune component which may be identified and isolated following the invention is a cytolytic T cell ("CTL" hereafter), specific for complexes of peptides derived from the identified molecule and MHC molecules to which these peptides bind, forming a complex. It is fairly well accepted that a CTL response involves the identification of complexes of MHC molecules and peptides, generally about 8–12 amino acids in length, but most preferably 9 or 10 amino acids in length, by T cell receptors ("TCRs") on the surface of circulating T cells. The TCRs react by binding to these complexes, setting in motion as it were a series of reactions including the proliferation of CTLs specific for these complexes. One can produce and/or isolate such CTLs using the method of the invention, plus further steps.

As is pointed out in the examples which follow as well as the disclosure in general, one can easily identify cDNA encoding an antigen of interest. Once this is identified, one uses the cDNA to transfect host cells which either already present desired MHC molecules on their surface, or which have been transfected with DNA encoding these MHC molecules. The cDNA for the molecule of interest is expressed, and the molecule is processed to antigenic peptides which are presented by MHC molecules, such as HLA molecules. CTLs directed against the complexes are obtained from lymphocytes, such as autologous lymphocytes. From responder cell populations, long-term CTL clones are then obtained by the well known technique of limiting dilution. Once a positive CTL response is observed, the specific peptides presented to the CTLs are identified using established methods for example, screening the previously identified CTL clones. Alternatively, the more recently described method of studying the sequence of the molecule of interest to identify potential MHC-binding motifs and then analyzing these peptides, first for binding to the relevant MHC molecule and then, if positive for MHC-binding, for their ability to generate CTLs recognizing the peptide MHC complex. Of course the peptides can also be eluted from the cells and sequenced, using well known techniques.

It will also be noted by the skilled artisan that one can correlate the expression of the molecule of interest back to a particular host cell or cells which expressed it. In so doing, one can remove the cDNA which expressed the molecule of interest, sequence it, and so forth. This aspect of the method is another feature of the invention.

Specific embodiments of the invention will be seen in the examples which follow. FIG. 1 depicts the method generally.

EXAMPLE 1

For the establishment of a cDNA library from human tissue total RNA was obtained from 0.5 g of a renal clear cell carcinoma and established according to the method of Chomzynski, J. Analyt. Biochem. 162: 156–159 (1987), incorporated by reference. The mRNA was extracted from total RNA with oligo-dT-cellulose. The synthesis of the first strand cDNA was accomplished by the method described by Gubler and Hoffmann, Gene 25: 263 (1983) using RNase H and DNA polymerase I. For adaptation of the cDNA Klenow enzyme, adaptors with EcoRI restriction enzyme sites were ligated to the cDNA ends using T4 DNA ligase (Ferretti L and Sgamerella V, Nucl. Acids Res. 9: 3695 (1981)). Following restriction enzymatic digestion with the enzyme XhoI, cDNA molecules of different length were separated using Sephacryl 400 and transfected into λZAPII phage vectors (Short JM et al., Nucleic Acids Res. 16: 7583 (1988)). The recombinant phage DNA was packed into phages after ligation with packing extracts and used for the transfection of $E.\ coli$ bacteria. The titration of the library resulted in $1.8 \times 10^6$ recombinant primary clones. The total cDNA library was transfected in $E.\ coli$ and amplified. The titer of the cDNA library after amplification was $10^{11}$ plaque forming units per ml (pfu/ml). These transfected cells were used in experiments which follow.

EXAMPLE 2

In accordance with the invention as described, supra, identification of immunogenic material was achieved by using human sera which has been completely depleted of antibodies directed against antigens derived from native and lytic λ phage-transfected $E.\ coli$ bacteria. To this end, the serum was "stripped" via absorption, as now described.

$E.\ coli$ bacteria of the strain XL1-blue were cultured in 50 ml LB medium overnight. After achieving an optical density of $OD_{600}=1.0$, the bacteria were pelleted by centrifugation, resuspended in 5 ml phosphate buffered saline (PBS), and sonicated by ultrasound. The bacterial lysate was bound onto a matrix of activated Sepharose, which was then put into a column and used for the absorption of the human serum. The serum was run over this column 10 times.

A culture of $E.\ coli$ XL1 blue bacteria in the exponential growth phase was pelleted by centrifugation, transfected in 0.01 M magnesium sulfate with $10^6$ λZAPII phages without a recombinant insert and incubated in 5 ml LB medium for four hours. The lysate of the transfected bacteria was used in the same manner as the untransfected bacteria, with the human serum described supra being passed through the column an addition ten times.

To complete the depletion of the serum, interfering antibodies from lytically transfected $E.\ coli$ bacteria were cultured on agar plates and their proteins were blotted onto nitrocellulose membranes after 10 hours of culture at 37° C. Following this, the serum which had been preabsorbed according to the above steps was transferred to the blotted nitrocellulose membrane, and the absorption procedure was repeated five times. The serum, which was processed in accordance with the invention, was totally depleted of antibodies directed against antigens derived from $E.\ coli$ and phages.

EXAMPLE 3

In this, a renal cancer-specific antigen was identified via the following steps. Bacteria of the strain XL1 blue were transfected with recombinant phages derived from the described cDNA library and plated at a density of $4-5 \times 10^3$ plaque forming units (pfu) per plate in LB-medium with isopropylthiogalactopyranoside ("IPTG"). After 12 hours of incubation at 37° C. nitrocellulose membranes were put on top of the cultures and culture plates were incubated for another four hours. This was followed by incubation of the nitrocellulose membrane for one hour in Tris-buffered saline (PBS) with 5% milk powder. After washing the nitrocellulose membranes three times in TBS, the stripped human serum secured following Example 2 was diluted 1:1000 in TBS/0.5% (w/v) milk power and incubated overnight with gentle shaking. After the incubation with the nitrocellulose membrane the serum was removed and kept for additional testing. Following incubation with serum, the nitrocellulose membranes were washed three times in TBS, and incubated with a polyclonal alkaline phosphatase-conjugated goat anti-human IgG serum for one hour. Following this, the nitrocellulose membranes were washed repeatedly with TBS/ 0.01% (v/v Tween 20). The reaction was developed using nitroblue tetrazolium chloride and bromochloro-indoyl-phosphate in TBS. The binding of human antibodies to the expressed protein became visible by a blue ring-formed color deposit on the nitrocellulose membrane. The efficient preabsorption of the serum made in possible to develop the membrane at 37° C. over several hours without compromising the quality of the test because of background reactivity caused by antibodies against E. coli and phage antigens.

Positive clones were localized on the agar plates, transferred into transfection buffer, and used for a second round of transfection and subcloning. A total of $1.8 \times 10^6$ recombinant clones were subjected to screening and five different positive-reacting clones were identified.

EXAMPLE 4

Figure 2:
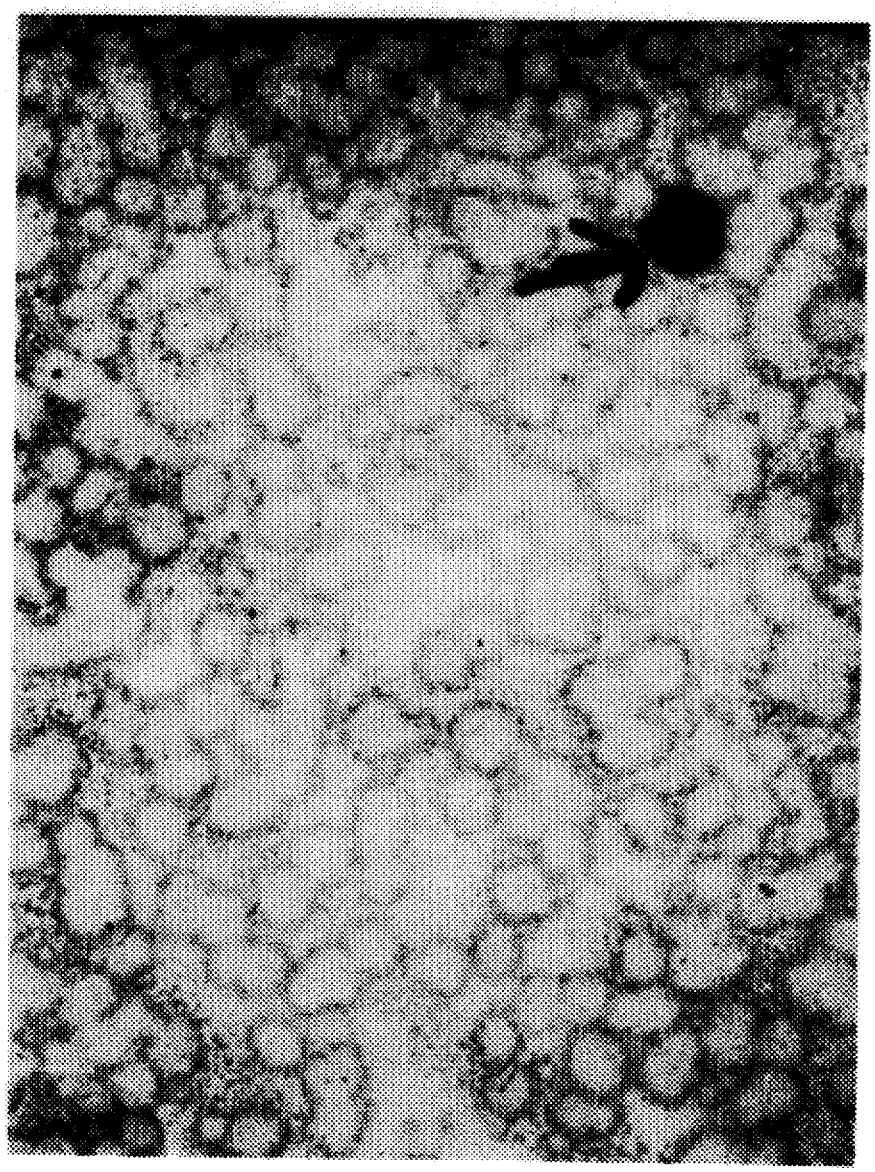
FIG. 2 shows a nitrocellulose membrane with a positive clone derived from the cDNA of a renal cell clear carcinoma that reacts with a 1:100 dilution of the patient's serum.
Figure 3:
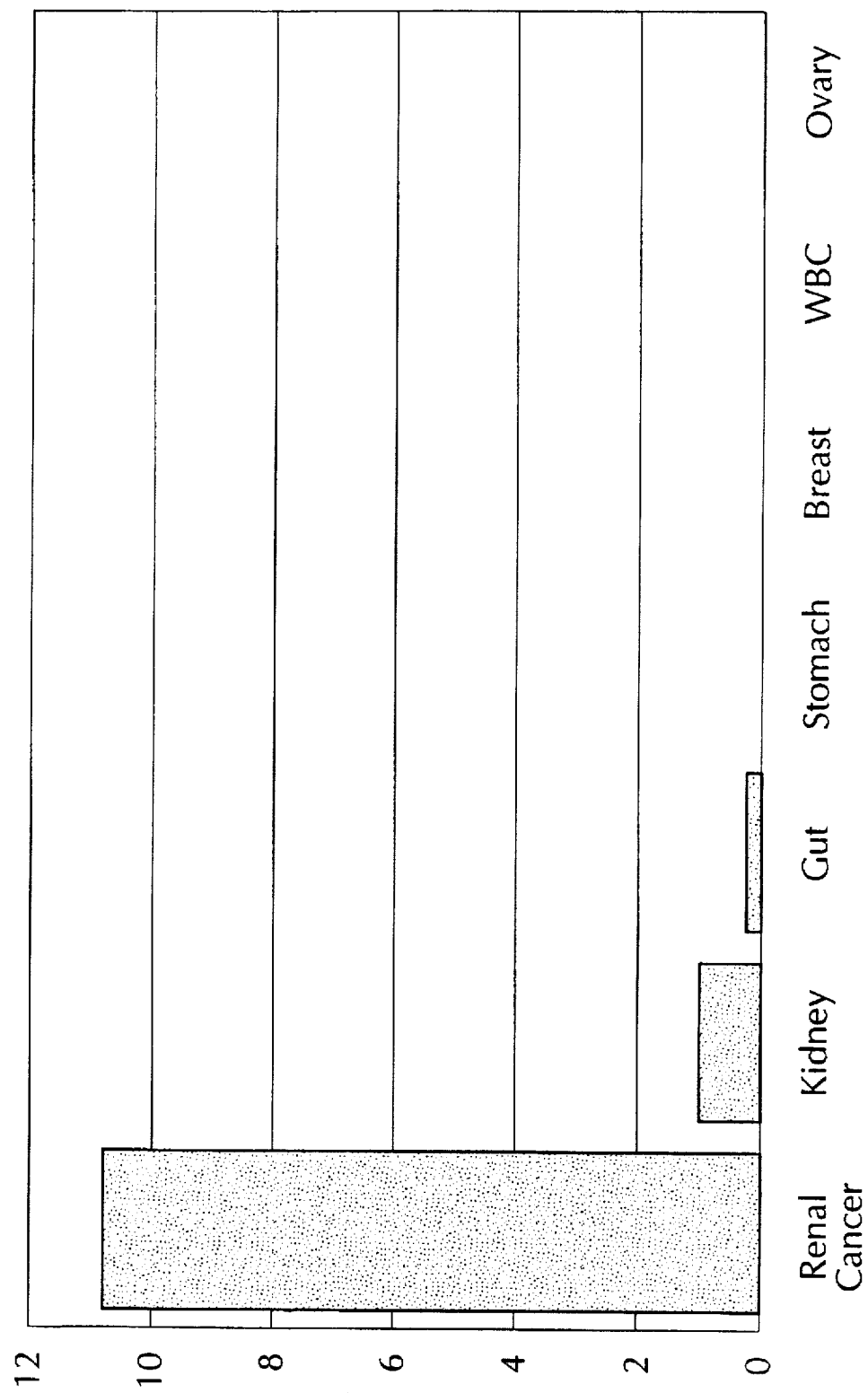
FIG. 3 shows, in bar graph form, the Northern Blot analysis of clone HOM-RCC-313 in renal cell carcinoma, normal kidney and other human tissues.

Positive clones secured following Example 3, i.e., those which had bound antibodies derived from the processed human serum, were subcloned to monoclonality by repeated rounds of transfection and testing of reactivity With the processed human serum. P-bluescript phagemids with the respective cDNA inserts were cloned by in vivo excision (Hay B and Short JM, Strategies 5: 16–19, 1992) from the λZAPII phage vectors and used for the transfection of E. coli SOLR bacteria. Plasmids were isolated from the bacteria after alkaline lysis with NaOH in a modification of the method of Birnboim HC and Doly J. J. Nucl. Acids Res. 7: 1513 (1979). The recombinant plasmid DNA was sequenced according to the classic method of Sanger (Proc. Natl. Acad. Sci. USA 74: 5463 (1977)) using M13-forward and M13-reverse oligonucleotides. The DNA sequence obtained and the resulting amino acid sequence were checked for in nucleic acid and protein data banks (Gene Bank, EMBL, Swiss Prot). The sequencing of the cDNA inserts was continued using internal oligonucleotides. Analysis showed no homology with any sequences deposited in the data banks. The full length cDNA clone referred to as SK313, which had been cloned with the RACE method (Frohman MA, Dush MK, Martin GR, Proc. Natl. Acad Sci. USA 85: 8998 (1988)), had a carbonic anhydrase domain at the 5' end. The nucleic acid sequence of this molecule is presented in SEQ ID NO: 1. FIG. 2 shows a nitrocellulose membrane with a positive clone from these experiments.

EXAMPLE 5

As a follow up to these experiments, RNA was isolated from a spectrum of malignant and normal human tissues according to the method of Chomyznski P, Sacchi N, Analyt Biochem. 162: 156 (1987). After denaturation, the total isolated RNA was separated on an agarose gel containing 1% formaldehyde by electrophoresis (Goldberg DA, Proc. Natl. Acad. Sci. USA 77: 5794 (1980)) and then blotted onto a nylon membrane according to a known method (Seed B, Nucl. Acids Res. 10: 1799 (1982)) Radiolabeled cDNA inserts of the identified clones were used for hybridization. The hybridization was carried out according to a known method (Geoffrey MW, Berger SI, Enzymol. 152: 419 (1987)). The presence of the respective RNA was demonstrated using autoradiography and X-ray films. The analysis demonstrated that the mRNA of clone HOM-RCC-313 was overexpressed in 4 out of 19 renal cell carcinomas compared to normal kidneys. Very weak expression was found only in colonic mucosal tissue and in normal kidney. Expression in other tissues could not be demonstrated.

EXAMPLE 6

To determine the incidence of antibodies against antigens which are identified in accordance with the invention, sera from healthy individuals and tumor patients were analyzed. To this end, the sera were processed as described, supra, and depleted from antibodies against antigens derived from E. coli and phages. For the detection of antigen-specific antibodies, phages derived from reactive clones were mixed with non-reactive phages derived from the same cDNA library at a ratio of 1:10 and tested as described supra for reactivity with antibodies in the human test serum. The serum which had been used for the identification of the antigen was used as a positive clone. The non-reactive phages served as a negative control. A serum sample was positive for antigen reactive antibodies, if the expected percentage of the phage plaques showed a positive reaction. In the case of the renal cell carcinoma antigen represented by clone HOM-RCC-313, the analysis of a spectrum of human sera showed that only sera from renal cell carcinoma patients contained reactive antibodies. Sera from healthy controls and patients with other tumors did not contain such antibodies.

The cDNA for clone HOM-RCC-313 was excised from the plasmid DNA by digestion with the restriction enzyme EcoR1, was separated by agarose gel electrophoresis, followed by extraction from the gel. This was then used to create a vector which expresses a fusion protein with the bacterial protein anthranilate synthetase. A relevant fragment in the exact open reading frame was cloned into pATH plasmid vectors (Koerner TJ, Hill JE, Myers AM, Tzagaloff A, Meth. Enzymol. 194: 477 (1991). Induction of protein expression was obtained after transformation of the plasmids into E. coli of strain BL21 as described (Spindler KR, Rosser DSE, Berk AG, J. Virol. 49: 132 (1984)). Expressed, fusion proteins were separated by SDS gel electrophoresis, excised from the gel, eluted and freeze dried. Rabbits were immunized by subcutaneous injection with 100 µg of the lyophilisate dissolved in Freund's adjuvant. Immunization was repeated three times at two-week intervals using Incomplete Freund's Adjuvant. The rabbits were bled and antiserum was obtained. The obtained antiserum was depleted from antibodies reactive with E. coli and phages in the manner as is described supra and tested for reactivity against the renal carcinoma antigen as described for the human serum. Reactivity was detected at dilutions of 1:>100,000.

EXAMPLE 7

The protocols set forth in the preceding examples were followed, using biopsied tissue taken from different subjects suffering from (i) malignant melanoma, (ii) astrocytoma, and (iii) Hodgkin's Disease. Table 1, which follows, summarized the results, including those obtained with the renal cancer study, set out in detail in Examples 1–6, supra.

TABLE 1

Antibody reactivity of autologous sera with recombinant clones derived from human tumor cDNA. cDNA libraries were screened with autologous patient serum. Positive clones were subcloned to monoclonality. Inserts from each clone were amplified with plasmid primers and separated by agarose gel electrophoresis. Southern blots were performed by cross hybridization with the respective inserts.

| tumor | clones tested | positive clones | different inserts |
|---|---|---|---|
| malignant melanoma | $1.0 \times 10^6$ | 40 | 10 |
| renal cell carcinoma | $1.8 \times 10^6$ | 7 | 5 |
| astrocytoma | $1.2 \times 10^6$ | 49 | 5 |
| Hodgkin's disease | $1.0 \times 10^6$ | 14 | 4 |

Following the analysis of the different inserts observed, the melanoma cells expressed the known tumor rejection antigen precursor MAGE-1 (see van der Bruggen et al., Science 254: 1643–7 (1991), incorporated by reference), as well as a new antigen. A portion of the cDNA sequence of this antigen is set forth in SEQ ID NO: 2.

When the astrocytoma study was completed, the observed insert corresponded to the previously described Tegt gene (Old, Canc. Res. 41: 361–375 (1981), incorporated by reference).

When the Hodgkin's Disease study was completed, a previously unknown antigen was isolated, and cDNA encoding it was identified in the library, using standard methods. The antigen is a newly observed, lectin-like structure, a portion of the cDNA for which is set forth in SEQ ID NO: 3. Also observed were antibodies against restin, described by Bilbe, et al, EMBO J 11: 2103–13 (1992). This is an intermediate filament associated protein, expression of which has been shown to be restricted to Hodgkin and Reed-Sternberg cells, as well as cultured monocytes.

EXAMPLE 8

A further study of occurrence of antibodies against the antigens described in Examples 1–7 was carried out. Table 2 summarizes these assays. In these studies, phages from positive clones were mixed with non-reactive phage (ratio:1:10), and then used to transfect bacteria (*e. coli*). Dilutions of patient sera (1:200), were used, in an enzyme linked immunosorbent assay (ELISA), as described supra. "HOM-MEL-40" refers to the new melanoma antigen (SEQ ID NO: 2), while "HOM-MEL-55" refers to MAGE-1 (van der Bruggen et al., supra). "HOM-RCC 3.1.3" is the renal cancer antigen of SEQ ID NO: 1. "HOM-GLO-30.2.1" refers to the previously identified astrocytoma associated antigen, "HOM-HD-21" refers to the new, lectin-like antigen of SEQ ID NO: 3, and "HOM-HD-397" is the previously identified restin antigen.

The fact that antibodies against the tumor antigens, excepting only restin, were detected, albeit at varying rates, only in the sera of patients diseased with the same type of tumor suggests that tumor growth is essential for the development of a humoral response against tumor antigens.

The reason for the presence of restin in healthy controls is not clear. One may speculate that tolerance against respective antigens might be circumvented, because the antigen may have similar sequences to another antigen, the donor may have premalignant cells, or the antigen may be activated in normal cells under non-malignant conditions, such as viral infections, or other inflammatory processes.

EXAMPLE 9

In order to determine the expression pattern of the newly identified antigens described herein, Northern blot analysis was carried out, using a variety of human tissues.

RNA was extracted from tissue samples (tumor and normal) using the well known guanidium isothiocyanate/phenol/chloroform method of Chomzynski, et al., supra. The RNA integrity was checked via electrophoresis in formalin/MOPS gels. Then, gels containing 40 ug of RNA per lane were blotted onto nylon membranes. These Northern blots were then probed with the cDNA of SEQ ID NO: 1, 2 or 3. Hybridization was with $^{32}P$ labelled probes at 42° C., with formamide. The filters were washed at 65° C., at 1×SSC, 0.2% SDS, and exposed for 16 hours. These are "stringent conditions" as defined hereafter. After exposure, filters were stripped and rehybridized with GAPDH.

Table 3 summarizes these results.

TABLE 2

Humeral immune responses against human tumor antigens. Phages from positive clones were mixed with nonreactive phages of the cDNA-library at a ratio of 1:10 and used to transfect bacteria. IgG antibodies to the clones were detected with an enzyme-linked assay using 1:200 diluted patient sera.
n.t. = not tested

| antigen identity/homology | HOM-MEL-40* | HOM-MEL-55 MAGE-1 | HOM-RCC-3.1.3* CAH-like | HOM-GLIO-30.2.1 tegt | HOM-HD-21* lectin-like | HOM-HD-397 restin |
|---|---|---|---|---|---|---|
| melanoma patients | 2/11 | 4/11 | n.t. | n.t. | n.t. | n.t. |
| renal cancer patients | 0/8 | 0/8 | 2/14 | 0/7 | 0/7 | 5/7 |
| astrocytoms patients | 0/10 | 0/10 | 0/11 | 2/13 | 0/11 | 7/11 |
| Hodgkin's patients | 0/10 | 0/10 | 0/17 | 0/17 | 10/18 | 14/17 |
| healthy controls | 0/12 | 0/12 | 0/15 | 0/20 | 0/17 | 12/17 |

TABLE 3

Expression pattern of tumor antigens in various tissues (selection).
Northern-blot analysis was performed with RNA samples from tumor and
normal human tissues matched by hybridization with GAPDH.
Expression ratios were calculated after densitometric analysis of autoradiographs.
The signal obtained with the normal counterpart of the diseased tissue was set to 1.
n.t. = not tested;

| antigen identity/homology | HOM-MEL-40* | HOM-RCC-3.1.3* CAH-like | HOM-GLIO-30.2.1 Tegt | HOM-HD-21* Lectin-like |
|---|---|---|---|---|
| kidney | — | 1 | 1.5 | — |
| brain | — | n.t. | 1 | n.t. |
| tonsil | — | — | 1 | 1 |
| stomach | — | — | 1.5 | — |
| colon mucosa | — | 0.2 | 1.5 | — |
| breast | — | — | 1.0 | — |
| renal cancer | — | >5 in 4/19 cases ≤1 in 15/19 cases | n.t. | — |
| Hodkin's tissue | n.t. | — | n.t. | >10 |
| astrocytoma | n.t. | n.t. | >5 in 8/12 1 in 4/12 | — |
| melanoma | ++ | — | n.t. | — |

As will be seen the new melanoma associated antigen is strongly expressed in melanoma, but not other tissues. Carbonic-anhydrase-like antigen was strongly expressed in about 20% of renal cell carcinomas, and only weakly in normal renal tissue. Tegt was overexpressed on 9/12 astrocytoma tissues compared to normal brain tissue. The mRNA for the lectin like molecule associated with Hodgkin's disease was increased about ten fold in diseased tonsils as compared to normal tonsils, suggesting that overexpression may be a frequent characteristic of proteins which elicit autologous B cell responses.

As the foregoing shows, the invention relates to a method for determining or isolating an immunoreactive substance. "Immunoreactive substance" as used herein refers to any material which provokes some form of immune response in the subject which produces it. This response may be based upon either a B cell or a T cell response. Such immunoreactive substances include proteins, peptides, glycoproteins, lipoproteins, peptide containing complexes (e.g., MHC/peptide complexes), antibodies, and so forth. To determine such substances, a cDNA library is prepared from cells of a subject, using well known, standard methods. The cDNA is then inserted into an appropriate vector, such as a eukaryotic cell specific virus or a phage (i.e., a bacterial virus), to form a transfecting/transforming library, which is then incorporated into a host cell. The host cells are treated so that they express the library component (cloned cDNA) they receive. The host cells are then lysed, so that the expressed material is available for further treatment.

The lysed material is then contacted with a "stripped" sample believed to contain an immunogenic binding partner for the immunoreactive substance. "Immunogenic binding partner" as used herein refers to any immune system associated material which binds to the target, i.e., the immunoreactive substance. Such binding partners include, but are not limited to, antibodies, T cells, cytokines, ligands, receptors, and so forth, as well as truncated portions of these molecules, complementary nucleic acid molecules, and so forth. Note that for some of these components, such as T cells, further steps including those recited herein are required.

The stripped sample, as indicated supra, has been treated by contact with both (i) non-transfected or transformed host cells, and (ii) host cells transfected or transformed with vectors which do not contain the pertinent cDNA.

The stripped sample is useful for identifying binding partner for the expressed material because many of the immune components which would otherwise interfere with the specific immunological reaction desired have been removed via the absorption steps described herein.

The identification of the expressed material may be followed by isolation of the cDNA encoding it. One can punch holes through a membrane placed on top of Petri dishes containing colonies of host cells thereby giving position on the solid phase, such as nitrocellulose membrane, used in the immune reaction. Each colony is based upon limited cDNA transfection, thereby facilitating isolation and identification of relevant cDNA.

The invention also relates to the isolated nucleic acid molecules of SEQ ID NO: 1, 2 or 3, which encode for molecules which are associated with particular conditions. In addition to their role as coding materials, these molecule can also be used as probes to identify cells expressing the relevant antigens, as it has been shown that these cDNA molecules (SEQ ID NO: 1, 2 and 3) are based upon mRNA which translated to the antigen.

Also a part of the invention are isolated nucleic acid molecules, the complementary sequences of which hybridize to one of SEQ ID NO: 1, 2 or 3, and which encode a protein equivalent to those encoded by SEQ ID NO: 1, 2 or 3. "Stringent conditions" as used herein, refers to conditions at least as stringent as hybridization at 50 $\mu$l/cm$^2$ of 3.5× SSC, 1×Denhardt's solution, 25 mM sodium phosphate buffer (pH 7.0), using a $^{32}$P-labelled probe, for 18 hours at 65° C., followed by four washes (one hour, each wash, at 65° C., 2×SSC, 0.1% SDS), and a final wash for 30 minutes at 1.0×SSC 0.2% SDS. The final wash can be changed to 0.5×SSC to 0.2×SSC, or even 0.1×SSC, and SDS can be lowered to 0.1% to increase stringency, if desired.

Other features of the invention will be clear to the skilled artisan and need not be reiterated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 2679 base pairs
        ( B ) TYPE: nucleic acid
        ( C ) STRANDEDNESS: double- stranded
        ( D ) TOPOLOGY: linear ( x i ) SEQUENCE DESCRIPTION: SEQ ID NO:1:

```
CGCGAAGATG  CCCCGGCGCA  GCCTGCACGC  GGCGGCCGTG  CTCCTGCTGG    50
TGATCTTAAA  GGAACAGCCT  TCCAGCCCGG  CCCCAGTGAA  CGGTTCCAAG   100
TGGACTTATT  TTGGTCCTGA  TGGGGAGAAT  AGCTGGTCCA  AGAAGTACCC   150
GTCGTGTGGG  GGCCTGCTGC  AGTCCCCCAT  AGACCTGCAC  AGTGACATCC   200
TCCAGTATGA  CGCCAGCCTC  ACGCCCTCG   AGTTCCAAGG  CTACAATCTG   250
TCTGCCAACA  AGCAGTTTCT  CCTGACCAAC  AATGGCCATT  CAGTGAAGCT   300
GAACCTGCCC  TCGGACATGC  ACATCCAGGG  CCTCCAGTCT  CGCTACAGTG   350
CCACGCAGCT  GCACCTGCAC  TGGGGAACC   CGAATGACCC  GCACGGCTCT   400
GAGCATACCG  TCAGCGGACA  GCACTTCTCC  GCCGAGCTGC  ACATTGTCCA   450
TTATAACTCA  GACCTTTATC  CTGACGACAG  NACTGCCAGC  AACAAGTCAG   500
AAGACCTCGC  TGTCCTGGGT  GCTCTCATTG  AGATGGGCTC  CTTCAATCCG   550
TCCTATGACA  AGATCTTCAG  TCACCTTCAA  CATGTAAAGT  ACAAAGGCCA   600
GGAAGCATTC  GTCCCGGGAT  TCAACATTGA  AGAGCTGCTT  CCGGAGAGGA   650
CCGCTGAATA  TTACCGCTAC  CGGGGGTCCC  TGATCACACC  CCCTTGCAAC   700
CCCACTGTGC  TCTGGACAGT  TTTCCGAAAC  CCCGTGCAAA  TTTCCCAGGA   750
GCAGCTGCTG  GCTTTGGAGA  CAGCCCTGTA  CTGCACACAC  ATGGACGACC   800
CTTCCCCCAG  AGAAATGATC  AACAACTTCC  GGCAGGTCCA  GAAGTTCGAT   850
GAGAGGCTGG  TATACACCTC  CTTCTCCCAA  GTGCAAGTCT  GTACTGCGGC   900
AGGACTGAGT  CTGGGCATCA  TCCTCTCACT  GGCCCTGGCT  GGCATTCTTG   950
GCATCTGTAT  TGTGGTGGTG  GTGTCCATTT  GGCTTTTCAG  AAGGAAGAGT  1000
ATCAAAAAAG  GTGATAACAA  GGGAGTCATT  TACAAGCCAG  CCACCAAGAT  1050
GGAGACTGAG  GCCCACGCTT  GAGGTCCCCG  GAGCTCCCGG  GCACATCCAG  1100
GAAGGACCTT  GCTTTGGACC  CTACACACTT  CGGCTCTCTG  GACACTTGCG  1150
ACACCTCAAG  GTGTTCTCTG  TAGCTCAATC  TGCAAACATG  CCAGGCCTCA  1200
GGGATCCTCT  GCTGGGTGCC  TCCTTGTCTT  GGGACCATGG  NCACCCCAGA  1250
GCCATCCGAT  CGATGGATGG  GATGCACTCT  CAGACCAAGC  AGCAGGAATT  1300
CAAAGCTGCT  TGCTGTAATT  GTGTGAGATT  GTGAAGTGGT  CTGAATTCTG  1350
GAATCACAAA  CCAACCATGC  TGGTGGGCCA  TTAATGGTTG  GAAAACACTT  1400
CCATCCGGGG  CTTTGCCAGA  GCGTGCTTTC  AAGTGTCCTG  GAAATTCTGC  1450
TGCTTCTCCA  AGCTTTCAGA  CAAGAATGTG  CACTCTCTGC  TTAGGTTTTG  1500
CTTGGGAAAC  TCAACTTCTT  TCCTCTGGAG  ACGGACATC   TCCCTCTGAT  1550
```

-continued

| | | | | |
|---|---|---|---|---|
| TTCCTTCTGC | TATGCAAAAC | CTTTAATCTG | CACCTTACAN | ACTCGGGGAC | 1600 |
| AAATGGGGAC | AGGAAGGATC | AAGTTGTAGA | GNAGAAAAAG | AAAACAAGAG | 1650 |
| ATATACATTG | TGATATATAT | TAGGGACACT | TTCACAGTCC | TGTCCTCTGG | 1700 |
| ATCACAGACA | CTGCACAGAC | CTTAGGGAAA | TGGCAGGTTC | AAAGTTCCAC | 1750 |
| TTCTTGGTGG | GGATGAGAAG | GGAGAGAGAG | CTAGAGGGAC | AAAGAGAATG | 1800 |
| AGAAGACATG | GATGATCTGG | GAGAGTCTCA | CTTCGGAATC | AGAATTGGAA | 1850 |
| TCACATTCTG | TTTATCAAGC | CATAATGTAA | GGACAGAATA | ATACAATAAT | 1900 |
| AAGTCCAAAT | CCAACCTCCT | GTCAGTGGAA | CAGTTATGTT | TTATACTCTA | 1950 |
| CAGATTTTAC | AAATANATGA | GGCTNGTTCC | TTGAAAANTG | TGTTGNNTTG | 2000 |
| CTGTNGTCCN | NTGGAGGAGA | CATGAGTTCC | GAGATGACCA | ACTCNNGCNT | 2050 |
| TGNATNCTNG | GAGGNAATAN | GGCAGAACCA | AAATGACTGT | AGAACTTATT | 2100 |
| CTCTGTAGGC | CAAATTTCAT | TTCAGCCACT | TCTGCAGGAT | CCTACTGCCA | 2150 |
| ACCTGGAATG | GAGACTTTTA | TCTACTTCTC | TCTCTCTGAA | GATGTCAAAT | 2200 |
| CGTGGTTTAG | ATCAAATATA | TTTCAAGCTA | TAAAAGCAGG | AGGTTATCTG | 2250 |
| TGCAGGGGGC | TGGCATCATG | TATTTAGGGG | CAAGTAATAA | TGGAATGCTA | 2300 |
| CTAAGATACT | CCATATTCTT | CCCCGAATCA | CACAGACAGT | TTCTGACAGG | 2350 |
| CGCAACTCCT | CCATTTTCCT | CCCGCAGGTG | AGAACCCTGT | GGAGATGAGT | 2400 |
| CAGTGCCATG | ACTGAGAAGG | AACCGACCCC | TAGTTGAGAG | CACCTTGCAG | 2450 |
| TTCCCCGAGA | ACTTTCTGAT | TGCACAGTCT | CATTTTGACA | GCATGAAATG | 2500 |
| TCCTCTTGAA | GCATAGCTTT | TTAAATATCT | TTTTCCTTCT | ACTCCTCCCT | 2550 |
| CTGACTCTAG | GAATTCTCTC | TTCTGGAATC | GCTTGAACCC | AGGAGGCGGA | 2600 |
| GGTTGCAGTA | AGCCAAGGTC | ATGCCACTGC | ACTCTAGCCT | GGGTGACAGA | 2650 |
| GCGAGACTCC | ATCTCAAAAA | AAAAAAAA | | | 2679 |

( 2 ) INFORMATION FOR SEQ ID NO:2:

( i ) SEQUENCE CHARACTERISTICS:
        ( A ) LENGTH: 931 base pairs
        ( B ) TYPE: nucleic acid
        ( C ) STRANDEDNESS: double-stranded
        ( D ) TOPOLOGY: linear ( x i ) SEQUENCE DESCRIPTION: SEQ ID NO:2:

| | | | | |
|---|---|---|---|---|
| ACTTTCTCTC | TCTTTCGATT | CTTCCATACT | CAGAGTACGC | ACGGTCTGAT | 50 |
| TTTCTCTTTG | GATTCTTCCA | AAATCAGAGT | CAGACTGCTC | CCGGTGCCAT | 100 |
| GAACGGAGAC | GACGCCTTTG | CAAGGAGACC | CACGGTTGGT | GCTCAAATAC | 150 |
| CAGAGAAGAT | CCAAAAGGCC | TTCGATGATA | TTGCCAAATA | CTTCTCTAAG | 200 |
| GAAGAGTGGG | AAAAGATGAA | AGCCTCGGAG | AAAATCTTCT | ATGTGTATAT | 250 |
| GAAGAGAAAG | TATGAGGCTA | TGACTAAACT | AGGTTTCAAG | GCCACCCTCC | 300 |
| CACCTTTCAT | GTGTAATAAA | CGGGCCGAAG | ACTTCCAGGG | GAATGATTTG | 350 |
| GATAATGACC | CTAACCGTGG | GAATCAGGTT | GAACGTCCTC | AGATGACTTT | 400 |
| CGGCAGGCTC | CAGGGAATCT | CCCCGAAGAT | CATGCCCAAG | AAGCCAGCAG | 450 |
| AGGAAGGAAA | TGATTCGGAG | GAAGTGCCAG | AAGCATCTGG | CCCACAAAAT | 500 |
| GATGGGAAAG | AGCTGTGCCC | CCCGGGAAAA | CCAACTACCT | CTGAGAAGAT | 550 |
| TCACGAGAGA | TCTGGACCCA | AAGGGGGGA | ACATGCCTGG | ACCCACAGAC | 600 |

```
TGCGTGAGAG  AAAACAGCTG  GTGATTTATG  AAGAGATCAG  CGACCCTGAG   650

GAAGATGACG  AGTAACTCCC  CTCAGGGATA  CGACACATGC  CCATGATGAG   700

AAGCAGAACG  TGGTGACCTT  TCACGAACAT  GGGCATGGCT  GCGGACCCCT   750

CGTCATCAGG  TGCATAGCAA  GTGAAAGCAA  GTGTTCACAA  CAGTGAAAAG   800

TTGAGCGTCA  TTTTCTTAG   TGTGCCAAGA  GTTCGATGTT  AGCGTTTACG   850

TTGTATTTTC  TTACACTGTG  TCATTCTGTT  AGATACTAAC  ATTTCATTGA   900

TGACGAAGAC  ATACTTAATC  GATATTTGGT  T                        931
```

( 2 ) INFORMATION FOR SEQ ID NO:3:

( i ) SEQUENCE CHARACTERISTICS:
    ( A ) LENGTH: 1692 base pairs
    ( B ) TYPE: nucleic acid
    ( C ) STRANDEDNESS: double- stranded
    ( D ) TOPOLOGY: linear ( x i ) SEQUENCE DESCRIPTION: SEQ ID NO:3:

```
GATCCCCCGG  GCTGCAGGAA  TTCGGCACGA  GCAAAGGACT  TCCTAGTGGG    50

TGTGAAAGGC  AGCGGTGGCC  ACAGAGGCGG  CGGAGAGATG  GCCTTCAGCG   100

GTTCCCAGGC  TCCCTACCTG  AGTCCAGCTG  TCCCCTTTTC  TGGGACTATT   150

CAAGGAGGTC  TCCAGGACGG  ACTTCAGATC  ACTGTCAATG  GGACCGTTCT   200

CAGCTCCAGT  GGAACCAGGT  TTGCTGTGAA  CTTTCAGACT  GGCTTCAGTG   250

GAAATGACAT  TGCCTTCCAC  TTCAACCCTC  GGTTTGAAGA  TGGAGGGTAC   300

TTGGTGTCCA  ACACGAGGCA  GAACGGAAGC  TGGGGGCCCG  AGGAGAGGAA   350

GACACACATG  CCTTNCCAGA  AGGGGATGCC  CTTTGACCTC  TGCTTCCTGG   400

TGCAGAGCTC  AGATTTCAAG  GTGATGGTGA  ACGGGATCCT  CTTCGTGCAG   450

TACTTCACAT  CTCGTCATGC  CCTGTCCACC  GTTGTGGACA  CCATCTCCGT   500

CAATGGCTCT  GTGCAGCTGT  CCTACATCAG  CTTCCAGCCT  CCCGGCGTGT   550

GGCCTGCCAA  CCCGGCTCCC  ATTACCCAGA  CAGNNNTCAT  CCACACAGTN   600

GCAGAGCGCC  CNCTGGACAG  ATGTCTCTAC  TCCCGCCATC  CCACCTATGA   650

TGTACCCCCA  CCCCGCCTAT  CCGATGCCTT  TCATCACCAC  CATTCTGGGA   700

GGGCTGTACC  CATCCAAGTC  CATCCTCCTG  TCAGGCACTG  TNCTGCCCAG   750

TGCTCANGAG  GTTCCACATC  NAACCTGTGC  NCTGGGAACC  ACATCGCCTT   800

CCACCTGAAC  CCCCGTTTTG  ATGAGAATGC  TGTGGTCCGC  AACACCCAGA   850

TCGACAACTC  CTGGGGGTCT  CAGGAGCGAA  GTCTGCCCCG  AAAAATGCCC   900

TTCGTCCGTG  GCCAGAGCTT  CTCAGTGTGG  ATCTTGTGTG  AAGCTCACTG   950

CCTCAAGGTG  GCCGTGGATG  GTCAGCACCT  GTTTGAATAC  AACCATCGCC  1000

TGAGGAACCT  GCCCACCATC  AACAGACTGG  AAGTGGGGGG  CGACATCCAG  1050

CTGACCATGT  GCAGACATAG  GCGGCTTCCT  GGCCCTGGGG  CCGGGGCTG   1100

GGGTGTGGGG  CAGTCTGGGT  CCTCTCATCA  TCCCCACTTC  CCAGGCCCAG  1150

CCTTTCCAAC  CCTGCCTGGG  ATCTGGGCTT  TAATGCAGAG  GCCATGTCCT  1200

TGTCTGGTCC  TGCTTCTGGC  TACAGCCACC  CTGGAACGGA  GAAGGCAGCT  1250

GACGGGGATT  GCCTCCTCAG  CCGCAGCAGC  ACCTGGGGCT  CCAGCTGCTG  1300

GAATCCTACC  ATCCCAGGA Y  GCAGGCACAG  CCAGGGAGAG  GGGAGGNGTG  1350
```

-continued

| | | | | | |
|---|---|---|---|---|---|
| GGCAGTGAAG | ATGAAGCCCC | ATGCTCAGTC | CCCTCCCATC | CCCCACGCAG | 1400 |
| CTCCACCCCA | GTCCCAAGCC | ACCAGCTGTC | TGCTCCTGGT | GGGAGGTGGC | 1450 |
| CTCCTCAGCN | CCTCCTCTCT | GACCTTTAAC | CTNACTCTCA | CCTTGCACCG | 1500 |
| TGCACCAACC | CTTCACCCCT | CCTGGAAAGC | AGGCCTGATG | GCTTCCCACT | 1550 |
| GGCCTCCACC | ACCTGACCAG | AGTGTTCTCT | TCAGAGGACT | GGCTCCTTTC | 1600 |
| CCAGTGTCCT | TAAAATAAAG | AAATGAAAAT | NCTTGTTGGC | AAAAAAAAA | 1650 |
| AAAAAAAAC | TCGAGGGGCN | NCCCNGTACC | CAATTCGCCC | TA | 1692 |

I claim:

1. Method for determining an auto-immunoreactive substance produced by a subject capable of eliciting an immune response comprising:
   (a) producing a cDNA library of a cell taken from said subject,
   (b) inserting said cDNA library into an expression vector,
   (c) transfecting said vector into a host cell to produce a transfected host cell,
   (d) culturing said transfected host cell to express said auto-immunoreactive substance,
   (e) lysing said transfected host cell to form a lysate,
   (f) contacting a sample of a body fluid taken from said subject which contains an immunologic binding partner for said immunoreactive substance with a sample of lysed, non-transfected host cells, to remove any immunologic binding partner from said sample which is specific for said non-transfected host cell, to produce a stripped body fluid sample,
   (g) contacting said stripped body fluid sample with a sample of lysed host cells transfected with the same vector into which said cDNA library has been inserted wherein said vector does not contain any library cDNA, to remove any immunologic binding partners specific for vector-produced antigens thereby producing a twice stripped body fluid sample,
   (h) contacting said twice stripped body fluid sample to the lysate of (e), whereby any immunologic binding partners specific for said auto-immunoreactive substance bind thereto, and
   (i) determining binding in (h) to determine said immunoreactive substance.

2. The method of claim 1, further comprising identifying the transfected host cell expressing said immunoreactive substance, and isolating the cDNA contained therein.

3. The method of claim 1, further comprising isolating any immunologic binding partner bound to said auto-immunoreactive substance.

4. The method of claim 1, wherein said host cell is *E. coli*.

5. The method of claim 1, wherein said vector is a viral vector.

6. The method of claim 5, wherein said viral vector is a eukaryotic virus based vector.

7. The method of claim 5, wherein said viral vector is a phage vector.

8. The method of claim 7, wherein said phage is lambda phage.

9. The method of claim 1, wherein said host cell is a prokaryote.

10. The method of claim 1, wherein said host cell is a eukaryote.

11. The method of claim 1, further comprising immobilizing said lysate of step (e) on a solid phase prior to contact with said twice stripped sample.

12. The method of claim 1, wherein said body fluid sample is serum.

13. The method of claim 1, wherein said immunologic binding partner is an antibody.

14. The method of claim 1, wherein said auto-immunoreactive substance is an antigen associated with cancer.

15. The method of claim 1, wherein said auto-immunoreactive substance is an autoimmune disease associated antigen.

16. The method of claim 1, wherein said auto-immunoreactive substance is produced by a pathogen.

* * * * *

UNITED STATES PATENT AND TRADEMARK OFFICE
CERTIFICATE OF CORRECTION

PATENT NO. : 5,698,396

DATED : December 16, 1997

INVENTOR(S) : Michael Pfreundschuh

It is certified that error appears in the above-identified patent and that said Letters Patent is hereby corrected as shown below:

In column 3, line 20-21, after "prokaryote" delete ". Then" and replace with -- , --.

In column 3, line 23, between "any" and "case" delete - - - - -.

In column 7, line 20, change "With" to -- with--.

In column 8, line 36, change "Incomplete" to --incomplete--.

In column 8, line 37, change "Adjuvant" to --adjuvant--.

In column 9, Table 2, in the third line of the first column, change "astrocytoms" to --astrocytoma-- .

In column 11, Table 3, in the eighth line of the first column, change "Hodkin's" to --Hodgkin's--.

Signed and Sealed this

Fifteenth Day of May, 2001

Attest:

NICHOLAS P. GODICI

Attesting Officer

Acting Director of the United States Patent and Trademark Office